United States Patent [19]

Kurz

[11] 4,443,190
[45] Apr. 17, 1984

[54] THERMOPLASTIC ORTHODONTIC ARCH WIRE RETAINING ANNULAR LIGATURE AND PROCESS

[76] Inventor: Craven H. Kurz, No. 6 North Star, Apt. 106, Marina del Rey, Calif. 90291

[21] Appl. No.: 341,515

[22] Filed: Jan. 21, 1982

Related U.S. Application Data

[63] Continuation-in-part of Ser. No. 316,880, Oct. 30, 1981, abandoned.

[51] Int. Cl.³ ............................................. A61C 7/00
[52] U.S. Cl. .................................................... 433/15
[58] Field of Search .................................. 433/10, 15

[56] References Cited

U.S. PATENT DOCUMENTS 3,193,930 7/1965 Bien ....................................... 433/15

Primary Examiner—Robert Peshock
Attorney, Agent, or Firm—Keith D. Beecher

[57] ABSTRACT

An orthodontic arch wire retaining elastic annular ligature and process is provided, the ligature being composed of thermo-plastic material which is initially heated to a softened condition, stretched, and allowed to cool while it is maintained in its stretched state. Heat is applied to the ligature after it has been attached to an orthodontic appliance on a tooth, which causes the ligature to shrink and firmly hold the arch wire in place.

1 Claim, 1 Drawing Figure

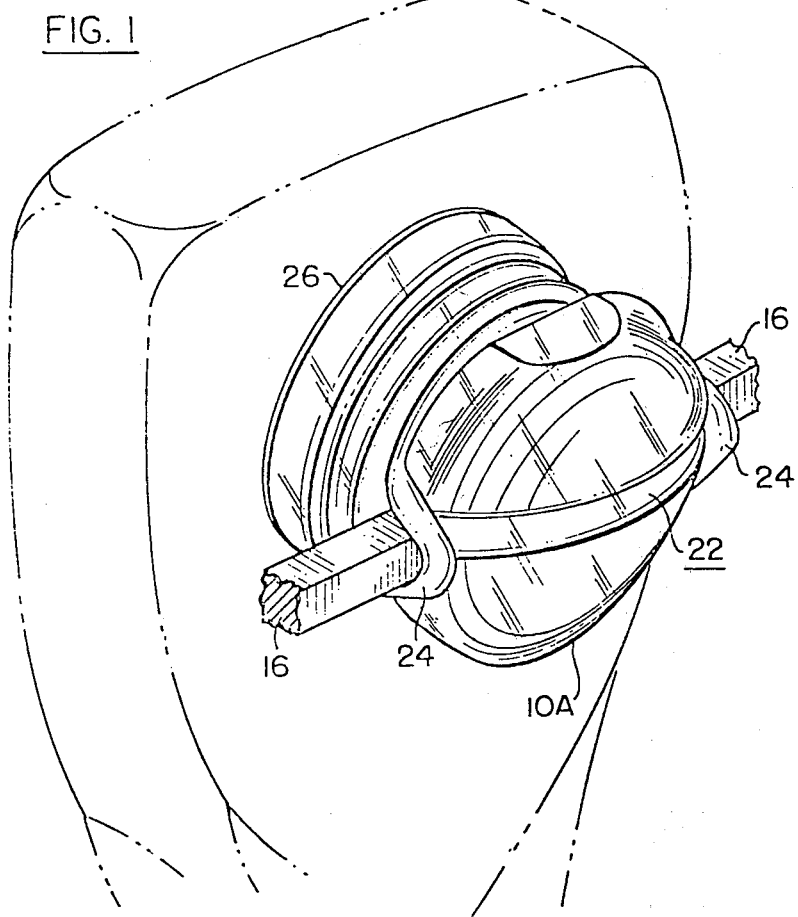

THERMOPLASTIC ORTHODONTIC ARCH WIRE RETAINING ANNULAR LIGATURE AND PROCESS

This application is a continuation-in-part of Copending Application Ser. No. 316,880 filed Oct. 30, 1981 and now abandoned in the name of the present inventor.

BACKGROUND OF THE INVENTION

It is usual in the orthodontic art to use a small annular elastic ligature, or tie wire, to hold the arch wire of an orthodontic appliance in place on each of the brackets which are mounted on the teeth of the patient. These ligatures are usually applied by hand or by the use of forceps or similar instruments to stretch the elastic ligatures and to insert the ligatures into annular support grooves in the brackets.

U.S. Pat. No. 4,277,236 which issued to the present inventor discloses an appropriate hand instrument by which such elastic ligatures may be applied simply and expeditiously in a stretched condition into the annular grooves in the orthodontic brackets and around the arch wire, so that the arch wire may be supported on the brackets.

In accordance with the concepts of the present invention, appropriate thermoplastic material is used to constitute the annular ligatures. The ligatures of the invention may be applied to the orthodontic brackets by hand, or by an instrument such as disclosed in said patent. The ligatures of the invention, as mentioned above, are heated by any appropriate means after they have been applied to contract and firmly and rigidly hold the arch wire on the brackets.

An appropriate material for the annular ligature of the invention is the same thermoplastic material which is used for shrink film packaging. In the practice of the invention, a ligature formed of the material is attached to an orthodontic appliance on a tooth of a patient, and it is then heated. This causes the ligature to shrink and firmly and securely hold the arch wire in place on the orthodontic bracket.

Almost any thermoplastic material, such as, polycarbonate, polyethylene, polypropylene, or the like, are suitable to constitute the ligature. In accordance with the usual shrink film techniques, the thermoplastic material is first heated to its softened state, stretched, and then allowed to cool while in the stretched state. Subsequent heating of a material while in the mouth of the patient, to a temperature not hot enough to burn the patient, causes the inherent memory of the material to cause the ligature to shrink to its original state and to remain in its shrunken state upon subsequent cooling, so that the ligature firmly and securely retains the arch wire in the orthodontic bracket, with a high strength and force as compared with the usual prior art elastic ligatures.

Suitable materials are glass-reinforced thermoplastics such as described, for example, in an article appearing in the Feb. 4, 1971—Sept. 3, 1971, issue of Machine Design entitled "Glass Reinforced Thermoplastic". The materials are presently being sold by LNP Corporation, of Malvern, Pennsylvania.

BRIEF DESCRIPTION OF THE DRAWINGS

FIG. 1 is a perspective representation of an orthodontic bracket supported on the tooth of a patient, and an arch wire supported on the bracket by an annular ligature which, in accordance with the present invention, is composed of appropriate thermoplastic material.

DETAILED DESCRIPTION OF THE ILLUSTRATED EMBODIMENT

An orthodontic bracket is designated 10A in FIG. 1, and it receives a usual orthodontic arch wire 16. The arch wire 16 is received in a transverse slot 22 extending across the bracket. The bracket also has a peripheral groove which receives an annular ligature 24 which serves to support the arch wire on the bracket.

In accordance with the present invention, ligature 24, as explained above, is composed of appropriate thermoplastic material, such as described above, and it is applied to the bracket 10A, either manually, or by an appropriate instrument. Then, the ligature is heated to an elevated temperature to cause it to shrink, and firmly and rigidly retain the arch wire 16 in the transverse slot 22.

In FIG. 1, the bracket 10A is affixed to the labial surface of the tooth by an adhesive layer 26. It is to be understood, of course, that the particular orthodontic bracket of FIG. 1 is shown merely by way of example, and that the ligatures of the present invention may be applied to any type of orthodontic bracket, either on the labial or lingual side of the teeth, to hold the arch wire in place on the bracket.

The annular ligature 24, in accordance with the present invention is formed of a thermoplastic material which has previously been heated to a softened state and stretched, and allowed to cool while it is maintained in its stretched state. The ligature is caused to shrink after it is in place by the application of heat so that the ligature serves to hold the arch wire 16 firmly in the transverse slot 22 on bracket 10A. This is achieved by heating the ligature, after it has been applied to the bracket, to a temperature at which it assumes a shrunken state, and allowing the ligature to cool while in its shrunken state.

The thermoplastic annular ligatures of the invention have a stronger pressure than the prior art elastic ligatures to pull the arch wire into the transverse slot on the bracket and, in so doing, results in better torque, tip and rotation control of the tooth. The thermoplastic annular bracket of the invention is similar in appearance to the elastic ligatures presently being used to hold the arch wire in the transverse arch wire slot of the bracket, but it exerts much more pressure for greater orthodontic effect.

The thermoplastic annular ligatures of the invention have less elasticity than the ligatures of the prior art and consequently maintain pressure on the arch wire for a more constant and prolonged period of time. Moreover, the annular ligatures of the invention are less permeable to the fluid of the mouth and are not as easily discolored as are the ligatures of the prior art.

An additional advantage of the thermoplastic annular ligatures of the invention is that they do not absorb food odors and mouth debris as readily as the prior art ligatures, and therefore maintain a more odor-free attachment for the orthodontic appliance.

The thermoplastic annular ligatures of the invention are smaller in cross-section when contracted than the prior art ligatures and consequently are smoother and offer less irritation to the tissues of the mouth. This feature serves to make the oral cavity easier to clean by usual oral hygiene measures. Also, this latter feature makes the thermo-elastic plastic ligatures less visible than the prior art ligatures and thus improves the aesthetics of the orthodontic appliance.

The invention provides, therefore, an orthodontic annular ligature which is easier and faster to attach than the prior art ligatures, and which is capable of exerting a higher and more even holding pressure on the arch wire than the prior art ligatures, and are less irritating to mouth tissues.

It will be appreciated that while a particular embodiment of the invention has been described, modifications may be made, and it is intended in the following claims to cover all modifications which come within the true spirit and scope of the invention.

What is claimed is:
1. A process for applying an annular thermoplastic ligature to an orthodontic appliance to hold an orthodontic arch wire firmly on the appliance and which comprises the steps of: heating the thermoplastic material to a softened state, stretching the material and allowing the material to cool while maintaining it in its stretched state; forming a ligature out of the thermoplastic material; applying the ligature to the appliance and around the arch wire; heating the ligature to a temperature at which the ligature assumes a shrunken state; and allowing the ligature to cool in its shrunken state firmly to hold the arch wire on the appliance.

* * * * *